United States Patent
Vogelsang et al.

(10) Patent No.: US 8,685,007 B2
(45) Date of Patent: Apr. 1, 2014

(54) METHOD AND DEVICE FOR FORMING CUT SURFACES IN A TRANSPARENT MATERIAL

(75) Inventors: Hartmut Vogelsang, Jena (DE); Dan Z. Reinstein, London (GB); Matthias Wottke, Leinburg (DE); Andre Narr, Saalburg (DE); Wilfried Bissmann, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 353 days.

(21) Appl. No.: 12/936,384

(22) PCT Filed: Apr. 2, 2009

(86) PCT No.: PCT/EP2009/002400
§ 371 (c)(1),
(2), (4) Date: Oct. 4, 2010

(87) PCT Pub. No.: WO2009/121593
PCT Pub. Date: Oct. 8, 2009

(65) Prior Publication Data
US 2011/0208171 A1    Aug. 25, 2011

(30) Foreign Application Priority Data
Apr. 4, 2008 (DE) .......................... 10 2008 017 772

(51) Int. Cl.
*A61F 9/01* (2006.01)
(52) U.S. Cl.
USPC .................................................. 606/5; 606/4
(58) Field of Classification Search
USPC .................................................. 606/130, 4–5
See application file for complete search history.

(56) References Cited

U.S. PATENT DOCUMENTS

| | | | |
|---|---|---|---|
| 5,984,916 A | 11/1999 | Lai | |
| 6,110,166 A | 8/2000 | Juhasz | |
| 6,902,561 B2 * | 6/2005 | Kurtz et al. | 606/4 |
| 7,101,364 B2 * | 9/2006 | Bille | 606/5 |
| 2003/0212387 A1 | 11/2003 | Kurtz et al. | |
| 2005/0107773 A1 | 5/2005 | Bergt et al. | |
| 2007/0179479 A1 | 8/2007 | Bille | |
| 2007/0179483 A1 * | 8/2007 | Muhlhoff et al. | 606/10 |
| 2007/0293851 A1 * | 12/2007 | Muhlhoff et al. | 606/11 |

FOREIGN PATENT DOCUMENTS

| | | |
|---|---|---|
| DE | 103 34 110 A1 | 2/2005 |
| EP | 1 591 087 A1 | 11/2005 |
| EP | 1 742 311 A1 | 1/2007 |
| WO | WO 98/14244 | 4/1998 |
| WO | WO 2005/011546 A1 | 2/2005 |
| WO | WO 2005/011547 A1 | 2/2005 |

\* cited by examiner

*Primary Examiner* — Bill Thomson
*Assistant Examiner* — Michael M Kim
(74) *Attorney, Agent, or Firm* — Christensen Fonder P.A.

(57) ABSTRACT

A method and a device for forming cut surfaces in a transparent material, particularly in the cornea, by producing optical breakthroughs in the material by application of laser radiation focused into the material. The focal point is adjusted in three dimensions to form the cut surface by the sequential arrangement of optical perforations. The focal point is guided in such a manner that cutting is divided into at least two steps, and in at least one of the steps, the formation of the cut is carried out with a path radius that decreases in size, and in one of the steps, the cut formation is carried out with a path radius that increases in size.

9 Claims, 3 Drawing Sheets

METHOD AND DEVICE FOR FORMING CUT SURFACES IN A TRANSPARENT MATERIAL

PRIORITY CLAIM

The present application is a National Phase entry of PCT Application No. PCT/EP2009/002400, filed Apr. 2, 2009, which claims priority from German Application Number 102008017772.5, filed Apr. 4, 2008, the disclosures of which are hereby incorporated by reference herein in their entirety.

FIELD OF THE INVENTION

The invention relates to a method for creating cutting planes in a transparent material, particularly in the cornea of the eye, through producing optical breakthroughs in the material by means of laser radiation focused on the material, whereby the focal point is preferably shifted three-dimensionally in order to form the cutting plane through sequentially arranged optical breakthroughs. The invention further relates to a device for creating cutting planes in a transparent material, particularly the cornea of the eye, with a laser radiation source, which focuses laser radiation into the material and effects optical breakthroughs therein, whereby a scan unit, which shifts the focal point three-dimensionally, and a control unit are provided, which controls the scan unit in order to form the cutting plane through sequentially arranged optical breakthroughs.

BACKGROUND

Cutting planes within a transparent material are generated, particularly, in laser-surgical methods, and especially in ophthalmic surgery.

Thereby, the treatment laser radiation within the tissue, i.e. beneath the tissue surface, is focused in such a way that optical breakthroughs in the tissue are formed.

Thereby, several processes initiated by the laser radiation occur in a time sequence in the tissue. If the power density of the radiation exceeds a threshold value, an optical breakthrough will occur, generating a plasma bubble in the material. After the optical breakthrough has been generated, said plasma bubble grows due to expanding gases. If the optical breakthrough is not maintained, the gas generated in the plasma bubble will be absorbed by the surrounding material and the bubble disappears again. However, this process takes very much longer than the forming of the bubble itself. If a plasma is generated at a material boundary, which may also be located within a material structure, material will be removed from said boundary.

This boundary phenomenon is then referred to as photoablation. In connection with a plasma bubble which separates previously connected material layers, the term photodisruption is usually applied. For the sake of simplicity, all such processes herein are collectively termed optical breakthrough, i.e. said term includes not only the actual optical breakthrough, but also the effects resulting therefrom in the material.

For high accuracy of a laser-surgical method, it is imperative to ensure high localization of the effect of the laser beams and preferably avoid collateral damage to adjacent tissue. It is therefore common in prior art to apply the laser radiation in pulsed form, so that the threshold value required for the triggering of an optical breakthrough is exceeded only during the individual pulses for the power density. In this regard, U.S. Pat. No. 5,984,916 clearly shows that the spatial extent of the optical breakthrough (in this case, the generated interaction) strongly depends on the pulse duration.

Therefore, high focusing of the laser beam in combination with very short pulses allows for placing of the optical breakthrough in a material with pinpoint accuracy.

The use of pulsed laser radiation has recently become established practice in ophthalmology, particularly for laser-surgical correction of defective vision.

Defective vision of the eye often results from the fact that the refractive properties of the cornea and the lens do not effect optimal focusing on the retina.

Aforementioned U.S. Pat. No. 5,984,916 as well as U.S. Pat. No. 6,110,166 describe generic methods of producing cuts by means of a suitable generation of optical breakthroughs, so that, ultimately, the refractive properties of the cornea are specifically influenced. A multitude of optical breakthroughs are sequentially arranged in such a way that a lens-shaped partial volume is isolated within the cornea of the eye. The lens-shaped partial volume, which is separated from the remaining corneal tissue, is then removed from the cornea through a laterally opening cut. The shape of the partial volume is selected in such a way that, after removal, the shape and, thus, the refractive properties of the cornea are modified in such a way that the desired correction of the visual defect is effected. The cutting planes required hereto are curved, which makes a three-dimensional shifting of the focus necessary. Therefore, a two-dimensional deflection of the laser radiation is combined with simultaneous shifting of the focus in a third spatial direction.

A further application of producing a cut by means of pulsed laser radiation in the cornea is the generation of so-called flaps, i.e., a cut which partially severs a small slice of the cornea in such a way that it can be folded back, making the underlying tissue of an ablation accessible by means of an excimer laser. Hereby, the desired cornea profile is produced through the ablation and the flap returned to its original position after treatment.

The two-dimensional deflection of the laser radiation is, similar to the focus shift, equally crucial for the accuracy with which the cutting plane can be produced. For the two-dimensional beam guidance, i.e., for the movement of the focus essentially in the plane of the cut, two strategies have been applies thus far. In DE 103 34 110, it is suggested to move the focus essentially in a closed path and to increase and/or decrease the path radius after each rotation by the value which approximately corresponds with the diameter of the focus. The generation of the cutting plane can therefore be effected alternatively from the inside out or from the outside in. The guidance of the focus on a spiral path is also described. In EP 1 591 087, it is suggested to start the cut on the outside and guide it inwards by means of a spiral-shaped path with steadily decreasing radius.

In the field, it has become apparent that both strategies do not lead to optimal results. While the vision of the patient immediately worsens with a cut from the inside out due to bubbles forming in the center, making it impossible for the patient to target the usually existing fixation marker and causing interfering eye movements, there are also problems with the cut from the outside in with regard to correctly applying the necessary opening cut on the cutting plane since the focus must once again be positioned in the peripheral area, where there are still bubbles from the previous cutting direction in the tissue, which make the exact positioning of the focus difficult.

SUMMARY OF THE INVENTION

Therefore, the invention is based on the task of designing a method and a device of the aforementioned type in which the generation of a cutting plane with improved quality can be effected.

According to the invention, the focal point is guided in such a way that the cutting direction is separated into at least two partial steps, and whereby the cutting direction is effected with decreasing path radius in at least one of the partial steps and the cutting direction is effected with increasing path radius in one of the partial steps.

The task is further solved with a device of the aforementioned type, wherein the control unit controls the scan unit in such a way that the focal point in a first section is guided with decreasing path radius and with increasing path radius in a second section.

It is particularly advantageous to first execute the cut in the inner section from the outside in and to subsequently cut the second section from the inside out, whereby an overlapping zone can be provided between the first and second section.

According to the invention, the cut of the second section can be immediately followed by the opening cut.

BRIEF DESCRIPTION OF THE DRAWINGS

In the following, the invention will be further explained by way of examples with reference to the drawing, whereby.

DETAILED DESCRIPTION

Figure 1:
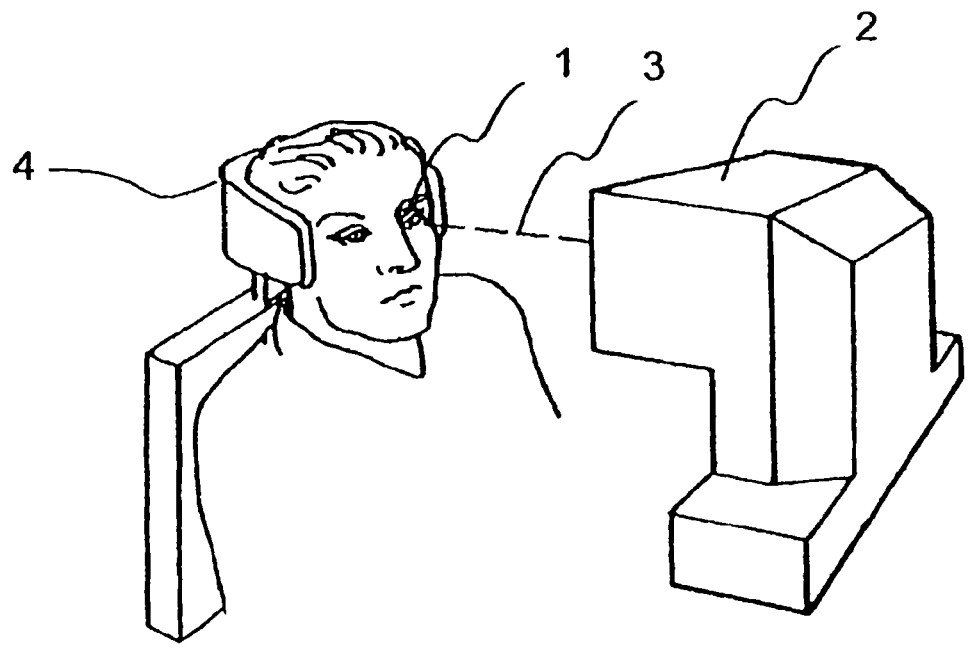
FIG. 1 is a perspective view of a patient during a laser-surgical treatment with a laser-surgical instrument.

FIG. 1 shows a laser-surgical instrument for treatment of an eye 1 of a patient, whereby the laser-surgical instrument 2 serves for the execution of a refractive correction. Thereto, the instrument 2 emits a treatment laser beam 3 onto the eye of the patient 1, whose head is immobilized in a head holder 4. The laser-surgical instrument 2 is capable of generating a pulsed laser beam 3, allowing for the execution of the method described, e.g., in U.S. Pat. No. 6,110,166.

Figure 2:
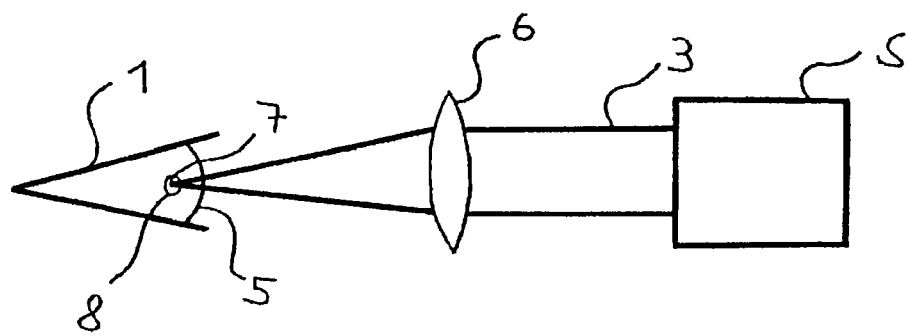
FIG. 2 depicts the focusing of a bundle of rays onto the eye of the patient with the instrument in FIG. 1.

Thereto, the laser-surgical instrument 2 exhibits, as schematically shown in FIG. 2, a beam source S, the radiation of which is focused on the cornea 5 of the eye 1. By means of the laser-surgical instrument 2, the defective vision of the eye 1 of the patient can be corrected in such a way that material is removed from the cornea 5 in such a way that the refractive properties of the cornea change by a desired degree. Thereby, the material is removed from the stroma of the cornea which lies below the epithelium and Bowman's membrane and above the Decemet's membrane and the endothelium. Alternatively, only one cut in the cornea for the preparation of a flap can be executed with the instrument 2.

The material removal and/or separation is carried out by separating tissue layers through focusing of the high-energy pulsed laser beam 3 by means of an objective telescope 6 in a focus 7 located in the cornea 5. Thereby, each pulse of the pulsed laser radiation 3 generates an optical breakthrough in the tissue, which initiates a plasma bubble 8.

As a result, the tissue layer separation covers a larger area than the focus 7 of the laser radiation 3. Through suitable deflection of the laser beam 3, many plasma bubbles 8 are now sequentially arranged during treatment. These adjacent plasma bubbles 8 then form a cutting plane 16.

Due to the laser radiation 3, the laser-surgical instrument 2 operates in the manner of a surgical knife which directly separates material layers within the cornea 5 without injuring the surface of the cornea 5. If the cut is guided up to the surface of the cornea 5 (opening cut) by generating further plasma bubbles 8, material of the cornea 5, isolated by the cutting plane 9, can be extracted laterally and, thus, removed and/or the flap partially lifted and folded back.

Figure 3:
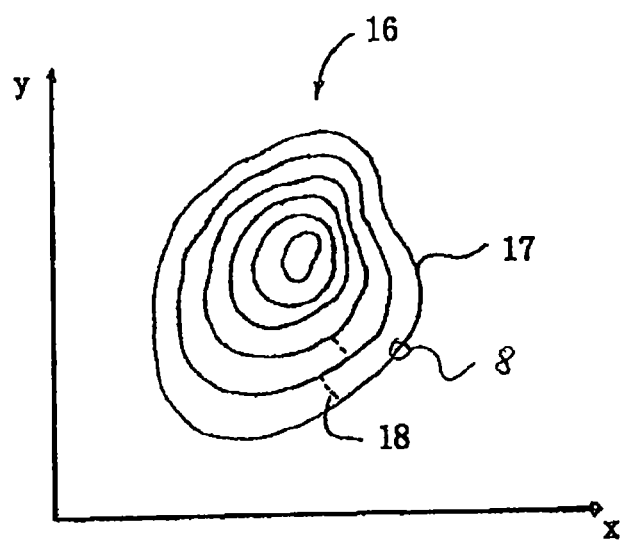
FIG. 3 depicts an example cross section.

The generation of the cutting plane 16 by means of the laser-surgical instrument 2 is schematically shown in FIG. 3. The cutting plane 16 is formed by sequential arrangement of the plasma bubbles 8, produced as a result of the continuous shift of the focus 7 of the pulsed focused laser beam 3, along the cutting line 17.

Thereby, the focus shift is effected, on the one hand, in an embodiment by means of a deflection unit in x and y, not shown in FIG. 2; on the other hand, the telescope 6 is suitably adjusted for a control in the z-direction. As a result, the focus can be adjusted along three orthogonal axes.

For the generation of the cutting plane 16, the focus 7 is adjusted through the deflection unit in accordance with the cutting lines 17, whereby the zoom optics 6 can, for each cutting line 17, adjust a respective z-coordinate for the focus 7. While the focus 7 passes over a cutting line 17, the telescope can remained fixedly adjusted, and only during the transitions 18, shown as dotted lines in FIG. 3, between the adjacent cutting lines 17 might an adjustment be required.

Figure 4:
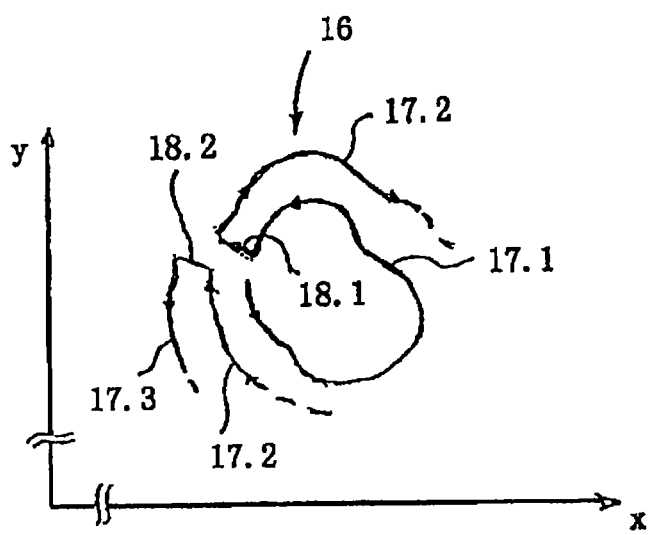
FIG. 4 depicts a segment of a cross section similar to FIG. 3 for clarification of the transition between subsequent cutting lines.

FIG. 4 shows the segment of the cutting line image 16. Every cutting line 17 is traced by the focus 7 as an almost completely closed curve, whereby the distance between beginning and end of the cutting line 17 does not exceed the allowable maximum distance between two plasma bubbles 8 as defined by a threshold value. At the end of each cutting line 17 (in FIG. 4, three cutting lines 17.1, 17.2, and 17.3 are indicated), a transition takes place to the respective next cutting line. As a result, a transition 18.1 between the cutting lines 17.1 and 17.2 and a transition 18.2 between the cutting lines 17.2 and 17.3 is provided. This continues for all cutting lines. Due to the transition such selected, the cutting lines 17 can be written as a cohesive path.

Figure 5:
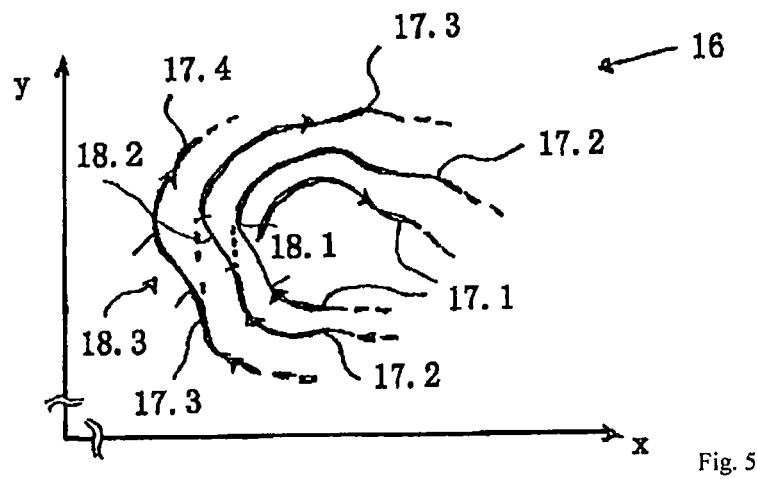
FIG. 5 depicts, similar to FIG. 4, a further option for a transition between the cutting lines, essentially in the form of a spiral.

In FIG. 4, the transitions 18 lie, essentially, on trajectories of the curved cutting plane 16. Thereto, FIG. 5 shows other transitions 18.1 to 18.3, whereby a sliding transition takes place between the end of one cutting line and the beginning of the immediately adjacent cutting line. For clarification, the continuation of the respective cutting lines, not followed by the focus 7, is shown as dotted line in FIG. 7. As can be seen, a sliding transition to the next cutting line takes place at the end of a contour line 17, whereby the cutting plane 16 is traced in the form of a spiral. For the generation of curved cutting planes, the telescope 6 is synchronously adjusted during the resulting transitions 18.1, 18.2, and 18.3. Alternatively, the telescope adjustment can essentially also be effected continuously over the entire cutting direction.

If the cutting direction is effected with increasing radius of the cutting line with regard to the previous cutting line, said cutting direction is called "from the inside out," and alternatively "from the outside in" in case of a decreasing radius.

Figure 6:
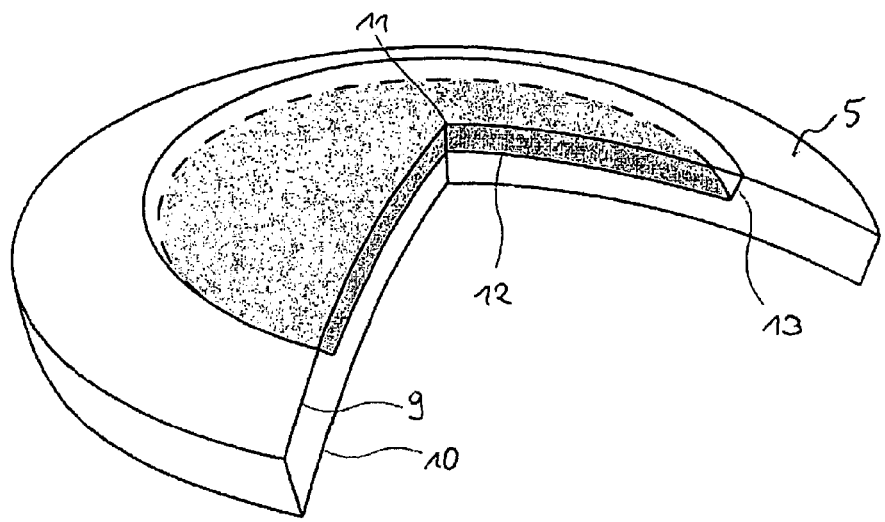
FIG. 6 depicts a schematic view of the cornea for classification of the segments.

In FIG. 6, the cornea of an eye is shown schematically. The cornea 5 exhibits a front of the cornea 9 and a back of the cornea 10. For the cutting of a flap 11, two cutting planes are commonly cut, the flap bottom 12 and flap edge 13. Thereby, the cutting plane of the flap bottom 12 runs somewhat parallel to the front of the cornea 9, and therefore with little adjustment of the focus in z-direction.

For the flap edge 13, a greater adjustment of the focus in z-direction is executed in order to guide the focus in several cutting lines from the flap bottom 12 to the front of the cornea 9 (opening cut).

According to prior art, the cutting of the flap bottom has always been executed in one direction, either from the inside out or from the outside in.

Figures 7A, 7B, 7C:
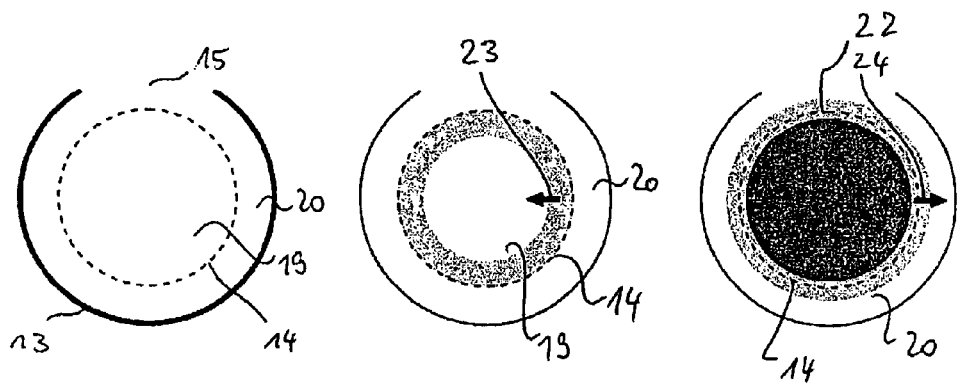
FIGS. 7a, 7b, and 7c depict a top view of the segments of the cutting plane.

The separation of the flap-bottom cut into two segments, according to the invention, is shown in FIG. 7a. The flap bottom 12 is separated through an imaginary separation 14 into two areas 19 (inner area) and 20 (outer area). Thereby, the separation 14 runs approximately 0.5 to 1.5 mm within the flap edge 13. The cut of the flap edge 13 is not executed completely; a hinge 15 remains which forms the connection between the flap 11 and the cornea 5, allowing for the flap 11 to be put back after treatment with the flap folded back. In a preferred embodiment, as shown in FIG. 7b, the flap bottom 12 is cut in the inner area 19 from the outside in (arrow 23), starting at the separation 14; then, as shown in FIG. 7c, the outer area 20 is cut from the inside out (arrow 24). Thereby, the cut for the outer segment can be applied at the separation 14. However, it has proven advantageous if said cut is initiated somewhat inside the separation 14, resulting in an overlap area 22. Once the focus 8 has reached the location of the flap edge 13, it can be cut immediately afterwards, whereby the focus 8 is correspondingly guided in the z-direction.

More than two segments can also be provided as can the cutting direction be varied without exceeding the scope of the invention.

The principle of the invention can also be applied for the cutting of so-called lenticules in the cornea, i.e., if more than one cut somewhat parallel to the front of the cornea 9 is executed in order to extract a lenticular part of the tissue.

Furthermore, an application of this method is also conceivable in more subjacent layers of the cornea. Particularly, this method can be applied for lamellar keratoplasty.

The invention claimed is:

1. A method of creating a curved cutting plane in a cornea of the eye, comprising:
    producing optical breakthroughs in the cornea of the eye by application of laser radiation focused into the cornea at a focal point;
    shifting the focal point three-dimensionally to form the cutting plane through sequentially arranged optical breakthroughs;
    guiding the focal point such that a cutting area is separated into at least two areas, including a first area and a second area;
    generating a cut with a decreasing path radius in the first area, thereby separating a first portion of a corneal material layer to be displaced from the eye; and
    generating a cut with an increasing path radius in the second area, thereby separating a second portion of the corneal material layer to be displaced from the eye;
    wherein the second area is radially outward from the first area.

2. The method according to claim 1, further comprising firstly executing the cut with the decreasing path radius in the first area in a first cutting direction; and secondly executing the cut with the increasing path radius in the second area in a second cutting direction, the first area defining an inside area, the second area defining an outside area, the first cutting direction being an inward direction, and the second cutting direction being an outward direction.

3. The method according to claim 2, further comprising providing an overlapping zone between the first area and the second area.

4. A device for creating curved cutting planes in the cornea of the eye, comprising:
    a laser radiation source that focuses laser radiation into the cornea at a focal point and therein causes optical breakthroughs;
    a scan unit that adjusts the focal point three-dimensionally;
    a control unit that controls the scan unit to form the cutting planes through sequentially arranging the optical breakthroughs in the cornea;
    wherein the scan unit for the adjustment of the focal point in one spatial direction comprises adjustable optics; and
    wherein the control unit controls the scan unit such that the focal point is guided in a first area with a decreasing path radius and in a second area with an increasing path radius and the second area is radially outward from the first area.

5. The device, according to claim 4, wherein the adjustable optics comprise a telescope arrangement.

6. The method of claim 1, further comprising displacing the corneal material layer from the eye.

7. The method of claim 6, wherein displacing the corneal material layer from the eye comprises removing the corneal material layer from the eye.

8. The method of claim 6, wherein the corneal material layer comprises a hinged flap, and displacing the corneal material layer from the eye comprises lifting the flap.

9. The method of claim 8, further comprising returning the flap to the eye after a treatment to the eye.

* * * * *